United States Patent [19]

Shernov

[11] Patent Number: 5,053,218

[45] Date of Patent: Oct. 1, 1991

[54] PRESSURIZED HAIR SPRAY COMPOSITION

[75] Inventor: Stephen Shernov, Long Valley, N.J.

[73] Assignee: Cosmosol, Ltd., White Plains, N.Y.

[21] Appl. No.: 381,053

[22] Filed: Jul. 17, 1989

[51] Int. Cl.⁵ ................................................ A61K 7/11
[52] U.S. Cl. ....................................... 424/47; 424/71; 424/DIG. 1; 424/DIG. 2
[58] Field of Search ............... 424/47, 70, 71, DIG. 1, 424/DIG. 2

[56] References Cited

U.S. PATENT DOCUMENTS

| | | | |
|---|---|---|---|
| 4,015,612 | 4/1977 | Pavlik et al. | 424/71 |
| 4,711,775 | 12/1987 | Dittmar et al. | 424/70 |
| 4,845,204 | 7/1989 | Lang et al. | 424/47 |
| 4,874,604 | 10/1989 | Sramek | 424/71 |

Primary Examiner—Thurman K. Page
Assistant Examiner—Susan S. Rucker
Attorney, Agent, or Firm—Walter Katz

[57] ABSTRACT

An environmentally sound, nonflammable pressurized hair-fixative spray product comprises shellac, dimethyl ether and water.

8 Claims, No Drawings

PRESSURIZED HAIR SPRAY COMPOSITION

BACKGROUND OF THE INVENTION

This invention relates to pressurized, aerosol formulations of fixative for hair finishing known as hair-holding sprays or simply hair sprays. Although hair sprays such as plunger sprays and rubber-bulb aerosol sprays are known for use by the individual, and compressed-air sprays are known for use at the professional beauty salon, the overwhelming proportion of commercially distributed hair sprays are sold as pressurized cans with finger-controlled valves built to deliver bursts of aerosols containing a hair fixative. The hair fixative composition normally contains a film-forming polymer, a plasticizer, a solvent, a perfume oil, one or more functional additives, and a propellant. The resin, the plasticizer, and the propellant are often comprised of mixtures.

The ideal hair spray composition is difficult to create because it should satisfy at least four sets of criteria. An environmentally sound hair spray composition would not contain a halocarbon propellant which is said to contribute to destruction of the earth's ozone layer. It would not contain a hydrocarbon propellant which would be flammable. It would not contain methylene chloride in the propellant because that compound may be carcinogenic, irritates the eye and skin, attacks the seal of the metal can, attacks the gaskets in the valve mechanism of the aerosol can, and may be a narcotic.

Although almost all commercial hair spray compositions contain ethanol as a solvent for the film-forming resin and plasticizers, that alcohol is disfavored because it can give beauticians, who are continuously exposed to it, upper respiratory infections, and irritations of the nose and skin. Alcoholic formulations are also dangerous because they are flammable.

The user wants a hair spray composition which gives good fixative properties, is easily washed out, is not tacky or gummy, has no irritating fumes, generates no static, functions well at high humidity, and is not expensive.

From the functional point of view on the hair, the spray composition should provide high curl retention, good combability, no flaking, good sheen and luster, no static charge, no heaviness or other resistance to combing, and no hair breakage or "split ends".

With the compositions hitherto known these sets of criteria are difficult to meet.

PRIOR ART

A standard compendium such as "Cosmetics: Science and Technology, vol. 2, 2d ed, published in 1972 by Wiley-Interscience, New York contains a large amount of background material and technology containing hair and hair-holding sprays. Chap. XIX is entitled "Shampoos"; Chap. XX "Hair-Grooming Preparations"; Chap. XXI "Permanent Waving"; Chap. XXII "Hair Straighteners"; Chap. XXII "Bleaches, Hair Colorings, and Dye Removers"; Chap. XXIV "Hair Conditioners, Lacquers, Setting Lotions, and Rinses"; Chap. XXVI "Aerosol Cosmetics"; and Chap. XXVII "Aerosol Hair Products".

In that treatise the compositions of many hair sprays, hair conditioners, and hair lacquers are given, often employing the same ingredients to impart their well-known functions. For example at page 354 a "basic formula" for a water-based, shellac hair spray is given as Formula 6:

| Concentrate | % |
| --- | --- |
| Refined, wax-free, bleached shellac | 15.00 |
| Borax, 10M | 3.45 |
| Water | 81.55 |
| adjust to pH 8.5 with ammonium hydroxide, then Above shellac-borax concentrate | 80.0 |
| Citroflex ™ A-2(Pfizer) plasticizer | 1.0 |
| Perfume | 0.2 |
| Water | 18.8 |

Shellac is the original, natural, film-forming polymer for hair sprays. Presumably it was used in the 1947 Argentine patent 59,548. The first synthetic polymer used in hair lacquers, fixatives, or hair sprays was poly(N-vinyl pyrrolidone), known for hair products at least since 1954. The hydroscopicity of PVP can be modified by employing a vinyl pyrrolidone/vinyl acetate copolymer. Other synthetic resins which are also useful include, poly(vinyl acetate), acrylic ester polymers, polyacrylic acids, poly(vinyl imidazole), cellulose ethers, vinyl acetate/crotonic acid copolymers, acrylic/sulfonamide/formaldehyde condensates, methyl vinyl ether/maleic anhydride copolymers, condensates of cyclohexanone, and linear polyesters. Many of these polymers, including shellac, have acidic pendant groups, which are made more water-soluble and benign for the consumer by being neutralized by ammonia, morpholine, or various amino-alcohols.

At page 356 of that treatise appears a water-based formula 7 for a hair-spray and an ethanol-based formula 10, as follows:

| | % |
| --- | --- |
| Formula 7 | |
| Gantrez ES-425 acidic copolymer (GAF), 50% | 19.62 |
| Ammonia, 28% | 1.89 |
| Water | 78.49 |
| Perfume and color | q.s. |
| Formula 10 | |
| Resyn 78-3305 (20% neutralized) (National Starch Co.) copolymer | 3.5 |
| Silicone oil SF-1075 (General Electric) | 0.2 |
| Plasticizing perfume oil | 0.4 |
| Ethanol qs | 100.0 |

The formulae above are for plunger hair-holding sprays or lacquers. At page 473 of the cited "Cosmetics" treatise appears the following for a classic shellac-type aerosol hair spray:

| Formula 1 | % |
| --- | --- |
| Dewaxed, unbleached shellac | 1.25 |
| Castor oil | 0.10 |
| Lanolin ester | 0.15 |
| Perfume oil | 0.15 |
| Ethanol, anhydrous SDA 40 | 28.35 |
| Fluorocarbon propellants 12/11(duPont Co.) 35:65 | 70.00 |

A typical synthetic polymer, alcoholic, aerosol formulation is given as Formula 3 on page 474 as follows:

| | % |
| --- | --- |
| Poly(vinyl pyrrolidone/vinyl acetate) 70/30 | 1.5 |

-continued

|  | % |
|---|---|
| Lanolin derivative | 0.05 |
| Silicone oil | 0.08 |
| Perfume Oil | 0.15 |
| Ethanol, anhydrous SDA 40 | 28.22 |
| Fluorocarbon propellants 12/11(duPont Co.) 35:65 | 70.00 |

Shellac can also be a plasticizer for a synthetic polymeric, alcoholic formulation, as shown on page 489 of the Wiley-Interscience 1972 treatise as Formula 1:

|  | % |
|---|---|
| Poly(vinyl pyrrolidone) 40,000 mol. wgt. | 4.0 |
| Shellac, dewaxed | 0.4 |
| Benzyl alcohol | 0.1 |
| Perfume oil | 0.2 |
| Ethanol, anhydrous | 95.3 |
| The concentrate mixture above | 40.0 |
| Fluorocarbon propellants 11/12(duPont Co.) 50:50 | 60.0 |

U.S. Pat. No. 3,207,386 discloses a non-flammable spray from a flammable propellant by using about 10–25 weight percent dimethyl ether to propel a variety of aqueous formulations such as window-cleaner, burn wound dressing, and a set for hair waving.

U.S. Pat. No. 4,243,548 discloses homogeneous mixtures of propellants and solvents which are single phase, minimize flammability and pollution, and are free of hydrocarbons and halohydrocarbon propellants. At least half of the mixture is non-combustible i.e. water, carbon dioxide, chlorinated hydrocarbons, and compounds having an ignition temperature above 600° C. The propellants are mixtures of methylene chloride, carbon dioxide, and dimethyl ether. The solvents for the cosmetic or medicinal agents are ketones, alcohols, esters, or halocarbons. Hair sprays are illustrated by conventional N-vinyl pyrrolidone and vinyl acetate copolymers 30:70.

U.S. Pat. No. 4,466,838 teaches a homogeneous tripartite propellant system of dimethyl ether, 2–3 carbon alcohol, and carbon dioxide for aqueous solutions, which does not give a flame jet.

U.S. Pat. No. 4,543,202 teaches a propellant consisting essentially of monochlorodifluoromethane, 1-chloro-1,1-difluoroethane, and dimethyl ether.

U.S. Pat. No. 4,767,613 teaches a terpolymer of N-vinyl pyrrolidone, t-butyl methacrylate, and either acrylic or methacrylic acid which can be formulated into a hair treating agent for aerosol administration propelled by volatile hydrocarbons, dimethyl ether, or mixtures thereof in an alcoholic or acetone solvent or mixture.

OBJECTS OF THE INVENTION

It is an object of this invention to provide a hair fixative, hair finishing, or hair-holding preparation in the form of an aerosol formulation which is free of ethanol or any other alcohol.

It is a further object of this invention to provide an aerosol hair spray which is not flammable.

It is yet another object of this invention to provide an aerosol hair spray based on a natural, film-forming, resin free of synthetic polymers or copolymers.

It is another object of this invention to provide an aerosol hair spray which is environmentally sound and which will not cause any respiratory problems or skin irritation to professionals who are exposed to it for a long period of time, and which is not potentially carcinogenic.

It is yet a further object to provide an aerosol hair spray which is not hydroscopic, tacky, or gummy, which has good curl retention, good countability, does not flake, has little static charge, good sheen, and has good hair-holding properties.

SUMMARY OF THE INVENTION

Surprisingly, the objects of this invention are met by a pressurized hair-fixative spray comprising shellac, dimethyl ether, and water. Preferably the composition comprises 1 to 15 wgt percent shellac, more preferably 4 to 10 wgt percent shellac, and most preferably 7.5 to 9.5 wgt percent shellac.

Preferably the dimethyl ether comprises from about 20 to about 40 wgt percent, more preferably about 30 to about 38 wgt percent, and most preferably 35 wgt percent. Except for additives, plasticizers, surface active agents, fragrances and neutralizers, the remainder of the charge to the aerosol fill is water, preferably 40 to 75 wgt percent.

DESCRIPTION OF THE PREFERRED EMBODIMENTS OF THE INVENTION

I have found that a superior, non-irritating, non-flammable, non-alcoholic, aerosol hair fixative can be formulated from shellac and water with dimethyl ether as the propellant. Shellac refers to all forms and grades of purified lac, which is the hardened resinous secretion of the female, small, scale insect *Laccifer Lacca* (Kerr) of the *coccidae* family. India, Burma, and Thailand are commercial sources.

Shellac has many grades and forms. In commerce there are two general types of products from the original seedlac: chemically bleached, white shellac and orange flake shellac. Each of these categories of product may be dewaxed to remove about 5 percent normal wax content. The dewaxed orange flake may also be decolorized. Grades intended for food, drug, or cosmetic use are further processed to meet FDA specifications. In comparison with synthetic polymers or copolymers of the addition type, the molecular weight of shellac is not as high, hence it may better be termed a resin. The molecular weight may be in the range of about 300 to about 3,000. All grades and types of shellac are useful in the present invention. Dewaxed grades are preferred, and foodgrade, bleached, dewaxed grades are more preferred. From 1 wgt percent to 15 wgt percent of the total content of the formulation is the preferred amount of shellac. From about 4 wgt percent to about 10 wgt percent is more preferred, and from 8 to 9 wgt percent is most preferred.

Shellac is a mixture of polyhydroxy, mostly aliphatic acids in the form of lactones, lactides, and inter-esters. The mean molecular weight of these compounds is about 1000. The acidic groups average $1.8 \times 10^{-5}$ in their ionization constants. For each carboxyl group, there are five hydroxyl and three ester groups.

Shellac is non-hydroscopic. It is made more water-soluble by neutralizing with mild bases such as ammonia, morpholine, dodecylamine, triisopropanolamine, aminomethylpropanol, aminomethylpropanediol, aminoethylpropanediol, or other bases such as borax. The presence of strong alkalis in the formulation would be detrimental to the hair. It is not desirable to neutralize the shellac totally because then the resulting film fixing the hair would not be resistant to high humidity. Ultimately the consumer wishes the hair fixative to be washable from the hair. The pH of the pressurized hair-fixative composition of the present invention may range from about 4 to about 11; from pH 6 to pH 8 is preferred. The neutralizing amine may be present from about 0.1 to 3 wgt percent of the total contents of the formulation. From about 0.6 to about 1.8 wgt percent is preferred. Most preferred is about 1.2 to about 1.4 wgt percent.

In order to avoid flaking of the film-forming polymer or too high a holding power, which might make the hair difficult to brush or comb, a plasticizer may be added to the formulation. The perfume oil may also function as a plasticizer for the resin, thus making it less brittle. There are numerous plasticizers for shellac including lanolins, silicones, benzyl alcohol or benzoate, glycerol, phosphate esters, citrate esters, polyethylene glycols, polypropylene glycols, as well as derivatives or mixtures of the above. Preferred plasticizers are polyethylene glycol 15, cocamine phosphate oleate, panthenol, lanolin, dimethylstearamine, polyethylene glycol 75, dimethicone copolyol, laureamide diethyl amine, coconut oils or other vegetable oils and perfume oils or fragrances. The useful range of plasticizer is from abut 0.5 to 5 wgt percent of the total amount of the formulation including propellant. From about 1 to about 3 wgt percent is preferred. Most preferred is from 1.5 to 2.5 wgt percent.

Various polypeptides or proteins such as collagen or its derivatives, or casein derivatives, or albumin derivatives can have a plasticizing function as well as adding the desired "crispness" to the film-forming resin as a fixative. Aliphatic esters in general such as the fatty isopropyl myristate or diisopropyl adipate can give added gloss to the hair as well as plasticizing the film-forming resin.

Other additives to the hair-fixative formulation include conventional perfumes, perfume oils, or fragrances as well as optionally antioxidants, antimicrobials, biocides, corrosion inhibitors, chelating agents, aloe plant extract, buffers to stabilize the pH, and coloring agents. Normally such additives range from about 0.1 to about 0.5 wgt percent of the total formulation including propellant.

The comparative flammability of pressurized aerosol formulations for the purpose of labeling is either: Nonflammable, Combustible, or Flammable. There are three tests for a pressurized product which determine which of the three ratings it receives: The flame extension test, an open-cup test, and a closed drum test. Since one of the main goals of the present invention is to achieve the status of "Nonflammable", the following criteria must be met.

1. Flame projection of under eight inches at full valve opening.
2. A flash point above 80° Fahrenheit.
3. No explosion when the product is sprayed through each of three specified openings in a 55-gal. closed drum in air under test conditions specified by the Chemical Specialty Manufacturing Aerosol Guide Book.

The key ingredient for the pressurized hair-fixative spray of the present invention to achieve the rating of Nonflammable resides in the fact that the preferred solvent is water. Small amounts of other nonaqueous solvents, such as water-soluble organic compounds, may be present but that condition is less preferred. Minor amounts of salts or other inert material may also be present, but that condition also is less preferred.

Water is the preferred solvent also for economic reasons. The preferred amount of water is from about 40 wgt to about 75 wgt percent of the total weight of the formulation.

The preferred propellant for carrying out the present invention is dimethyl ether. Small amounts of other propellants may also be present but that condition is less preferred. At ambient temperature (25° C./70° F.) dimethyl ether is 35 percent soluble in water and water is 6 percent soluble in dimethyl ether. Under pressure that situation is different, but the preferred amount of propellant in the present invention is 35 wgt percent of the total contents, that is concentrate plus propellant. Less preferred is from about 25 wgt percent to about 38 wgt percent of the total contents of the product, that is concentrate plus propellant. A useful range of dimethyl ether is from about 20 wgt percent to 40 wgt percent. Small amounts of other propellants such as hydrocarbons or chlorofluorocarbons may be employed, but they detract from the environmental soundness of or add to the flammability of the formulation of the present invention.

EXAMPLE 1

This Example illustrates but does not limit the scope of the instant invention.

Into a one-liter glass beaker the following materials were added:

85 g. food-grade, bleached shellac (Bradshaw Praeger Co., Chicago).

13 g. 2-amino-2-methyl-1-propanol.

20 g. polyethylene glyco/cocamine phosphate oleate (Lanatex Co.). Elizabeth, N.J.

2 g. rose oil fragrance.

530 g. deionized water.

This mixture was stirred at 120 rpm with a Lightning TM brand mixer for one hour until clear and uniform.

Then 150 g of the above concentrate was poured into each of four "8 oz" (53 mm × 185 mm) aluminum cans (300 ml) from the Boxal Co., Cranbury, N.J.

Employing a one-liter gas buret (J.G. Machine Co., Little Ferry, N.J.) 75 g of dimethyl ether (duPont Co., Wilmington, Del.) was then added to each can, which had previously been fitted with a one-inch Precision (Yonkers, N.Y. ??) Aquasol TM valve, having a 2×0.020-inch stem, a 0.014-inch orifice, a stainless steel spring, a 2×0.010-inch×0.0135-inch insert, a 0.060-inch capillary dip tube, and a butyl rubber hexagonal gasket.

Each container was then fitted with a Precision Co. KOSMOS TM actuator with a 0.020-inch exit orifice.

A test spray was made for each container to ensure an eight-can diameter conical spray at a distance of 27 cm (one foot). The spray rate was about 1 g/second.

After the test spray, each container was capped with a Berry Co. (Evansville, Ind.) 53-DSA 53-mm double shell plastic closure.

EXAMPLE 2

The pressurized hair-fixative aerosol spray, as produced in Example 1, is then tested for percent curl retention, as follows.

A standard hair swatch sample is prepared from 3 g. of 30-cm hair tress bound tightly at one end with a string. This swatch is shampooed, rinsed, and damp-dried with paper towels. Drying is then completed with a conventional hair drier at a distance of 27 cm for 15 minutes, followed by warming in an oven at 40° C. for another 15 minutes, and combed.

The swatch is then sprayed at a distance of 27 cm for 10 seconds with the spray from the product of Example 1, with movement of the spray up and down from all sides. Then the swatch is combed twice, rolled on an open mesh hair roller, and secured with a conventional roller clip. This curled swatch is then dried with a conventional hair drier at a distance of 14 cm for 15 minutes.

The dried, curled swatch is then removed from the curler and the distance measured from the tie at one end to the bottom of the curl. Then the suspended swatch is placed in a chamber at a constant humidity of 96–98 percent relative humidity at 78° F. for ten minutes. Upon removal from the chamber, the length from the tie to the bottom of the curl is measured again.

Employing the product of Example 1 on ten different hair samples, it is found that percent curl retention varies from 78 to 87 percent.

Also the combability, the feel, sheen, luster, flaking after two combings, and amount of static charge are all evaluated and found to be satisfactory.

The Examples and Specification above are intended to disclose some of the aspects of the present invention. Other variations will be apparent to those skilled in the art of formulating products for hair care, and these variations are still within the scope of the present invention, as measured by the Claims for Letters Patent enumerated below:

I claim:

1. A non-flammable, alcohol-free, environmentally-benign, carcinogen-free, one-liquid phase, pressurized hair-fixative spray product consisting essentially of
    a) shellac in the amount of about 7.5 to about 9.5 weight percent of the total fill;
    b) a neutralizer for said shellac in the amount of about 1.4 to 3 weight percent of the total fill;
    c) dimethyl ether in the amount of about 30 to about 38 weight percent of the total fill; and
    d) water in the amount of the rest of the total fill; whereby the hair is kept moist, the applied and consumer kept free of respiratory irritation, and the air unchanged.

2. A spray product as in claim 1, wherein the shellac is selected from the group consisting of seed lac, bleached white shellac, dewaxed bleached white shellac, orange flake shellac, dewaxed orange flake shellac, decolorized dewaxed orange flake shellac, food grade shellac, cosmetic grade shellac, and mixtures thereof.

3. A pressurized hair-fixative spray product as in claim 1, further including a plasticizer in an amount of about 0.5 to about 5 weight percent of the total fill.

4. A pressurized hair fixative spray product as in claim 3, wherein the plasticer is selected from the group consisting of polyethylene glycols and derivatives thereof, polypropylene glycols and derivatives thereof, citrate esters, coconut and other vegetable oils, lanolins, silicones, benzyl alcohol, benzyl benzoate, glycerol, proteins, polypeptides, phosphate esters, and mixtures thereof.

5. The pressurized hair fixative spray product as in claim 3, wherein the plasticizer comprises about 1 to about 3 weight percent of the total fill.

6. The spray product as in claim 1, wherein said neutralizer for the shellac is selected from ammonia, morpholine, dodecylamine, triisopropanolamine, 2-amino-2-methyl-1-propanol, aminomethylpropanediol, aminoethylpropanediol and borax.

7. The spray product as in claim 1, wherein the pH of the fill is about 9.

8. The pressurized hair-fixative product of claim 1 which also includes about 0.1 to about 0.5 weight percent of the total fill of one or more of each of the additives selected from the group consisting of a perfume oil, a fragrance, an antimicrobial agent, a biocidal agent, a buffer, an antioxidant, a chelating agent, an anticorrosive agent, aloe plant extract, a coloring agent, or mixtures thereof.

* * * * *